United States Patent
Kobylka et al.

(10) Patent No.: US 11,279,670 B2
(45) Date of Patent: Mar. 22, 2022

(54) PROCESS FOR SEPARATING AN ORGANIC ISOCYANATE

(71) Applicant: Covestro Deutschland AG, Leverkusen (DE)

(72) Inventors: Manfred Kobylka, Burscheid (DE); Michael Merkel, Düsseldorf (DE); Dominik Duerig, Aachen (DE); Bernhard Seidel, Leverkusen (DE)

(73) Assignee: Covestro Deutschland AG, Leverkusen (DE)

( * ) Notice: Subject to any disclaimer, the term of this patent is extended or adjusted under 35 U.S.C. 154(b) by 0 days.

(21) Appl. No.: 17/146,628

(22) Filed: Jan. 12, 2021

(65) Prior Publication Data
US 2021/0171450 A1    Jun. 10, 2021

Related U.S. Application Data

(62) Division of application No. 16/499,357, filed as application No. PCT/EP2018/058089 on Mar. 29, 2018, now Pat. No. 10,919,845.

(30) Foreign Application Priority Data

Apr. 3, 2017   (EP) ..................... 17164492
Apr. 12, 2017  (LU) ..................... 100164

(51) Int. Cl.
*B01D 53/14*  (2006.01)
*B01D 53/18*  (2006.01)
(Continued)

(52) U.S. Cl.
CPC .......... *C07C 263/20* (2013.01); *B01D 5/0027* (2013.01); *B01D 5/0087* (2013.01);
(Continued)

(58) Field of Classification Search
CPC .. C07C 263/20; B01D 5/0027; B01D 5/0087; B01D 53/14; B01D 53/18; B01D 53/185
See application file for complete search history.

(56) References Cited

U.S. PATENT DOCUMENTS

| | | |
|---|---|---|
| 4,847,408 A | 7/1989 | Frosch et al. |
| 8,692,016 B2 | 4/2014 | Sanders et al. |
| (Continued) | | |

OTHER PUBLICATIONS

Perry, Robert H., Perry's Chemical Engineers' Handbook, 7th ed., Chapter 14, McGraw-Hill, 1998.

*Primary Examiner* — Robert A Hopkins
(74) *Attorney, Agent, or Firm* — John E. Mrozinski, Jr.

(57) ABSTRACT

Provided is a process for separating an organic isocyanate prepared by reacting an organic amine with a stoichiometric excess of phosgene in the gas phase from the gaseous crude product obtained in the reaction, the process comprising the steps of (i) at least partially condensing the crude product stream containing at least the isocyanate, hydrogen chloride and unconverted phosgene by contacting with at least one liquid stream containing at least one quench liquid in a first separation apparatus to obtain a liquid stream containing at least some of the quench liquid and some of the isocyanate and a gas stream containing at least hydrogen chloride, evaporated quench liquid and phosgene, (ii) discharging the liquid stream obtained in step (i) via a first liquid outlet and of the gas stream obtained in (i) via a first gas conduit and (iii) at least partially condensing and/or absorbing the gas stream discharged in step (ii) through the first gas conduit, wherein that the at least partial condensation and/or absorption is effected in step (iii) by direct introduction of at least one cooling fluid, wherein the cooling fluid is introduced directly into the first gas conduit via at least one addition unit assigned to the first gas conduit.

6 Claims, 2 Drawing Sheets

(51) Int. Cl.
  *C07C 263/20* (2006.01)
  *B01D 5/00* (2006.01)
  *B01D 53/00* (2006.01)
  *B01F 3/04* (2006.01)

(52) U.S. Cl.
  CPC ........... *B01D 53/002* (2013.01); *B01D 53/14* (2013.01); *B01D 53/1487* (2013.01); *B01D 53/18* (2013.01); *B01D 53/185* (2013.01); *B01F 3/04049* (2013.01); *B01D 2252/205* (2013.01)

(56) References Cited

U.S. PATENT DOCUMENTS

| | | | |
|---|---|---|---|
| 8,765,991 B2 * | 7/2014 | Kintrup | C07C 263/10 558/302 |
| 9,932,299 B2 * | 4/2018 | Steffens | C07C 263/20 |
| 2003/0013909 A1 | 1/2003 | Leimkuhler et al. | |
| 2003/0069441 A1 | 4/2003 | Leimkuhler et al. | |
| 2003/0114705 A1 | 6/2003 | Friedrich et al. | |
| 2004/0068137 A1 | 4/2004 | Heiko et al. | |
| 2004/0167354 A1 | 8/2004 | Biskup et al. | |
| 2005/0137417 A1 | 6/2005 | Meyn et al. | |
| 2008/0167490 A1 | 7/2008 | Pohl et al. | |
| 2008/0000722 A1 | 8/2008 | Winslow et al. | |
| 2009/0221846 A1 | 9/2009 | Wolfert et al. | |
| 2012/0123152 A1 | 5/2012 | Bruns et al. | |
| 2015/0368190 A1 | 12/2015 | Steffens et al. | |

\* cited by examiner

PROCESS FOR SEPARATING AN ORGANIC ISOCYANATE

CROSS-REFERENCE TO RELATED APPLICATIONS

This application is divisional of U.S. Pat. No. 10,919,845, filed Sep. 30, 2019 as Ser. No. 16/499,357, which is a national stage application under 35 U.S.C. § 371 of PCT/EP2018/058089, filed Mar. 29, 2018, which claims the benefit of European Application No. 17164492.5, filed Apr. 3, 2017, and Luxembourg Application No. 100164, filed Apr. 12, 2017, all of which are incorporated herein by reference.

FIELD OF THE INVENTION

The invention relates to a cleaning apparatus for separating an organic isocyanate prepared by reacting an organic amine with a stoichiometric excess of phosgene in the gas phase from the gaseous crude product obtained in the reaction, comprising a first separating unit having at least a crude product inlet for a gaseous crude product stream containing at least the isocyanate, hydrogen chloride and unconverted phosgene, a first liquid inlet for a liquid stream containing at least a quench liquid and a first liquid outlet for a liquid stream containing at least some of the quench liquid and some of the isocyanate, wherein a gas conduit for conveying a gas stream containing at least hydrogen chloride, evaporated quench liquid and phosgene departs from the first separation unit. The invention also relates to a process for cleaning product streams containing organic isocyanates from a quench zone of the gas phase phosgenation. The invention further relates to a gaseous mixture for treatment in a wash column.

BACKGROUND OF THE INVENTION

There have long been general descriptions in the prior art of the preparation of organic isocyanates, especially diisocyanates, in the gas phase, which is utilized industrially, particularly for the production of tolylene diisocyanate, hexamethylene 1,6-diisocyanate, isophorone diisocyanate and diisocyanatodicyclohexylmethane. In all processes, a gaseous crude product is obtained that comprises at least isocyanate, hydrogen chloride and unconverted phosgene (phosgene is always used in excess), and which has to be subjected to further workup in order to obtain the desired isocyanate in pure form.

WO 2007/014936 A2, Method for producing isocyanates (in the gas phase), describes a quench zone in which the gaseous crude product is cooled down rapidly by injecting a quench liquid. In this quench zone, the reaction mixture consisting essentially of the isocyanates, phosgene and hydrogen chloride is mixed vigorously with the liquid injected. The mixing is effected in such a way that the temperature of the reaction mixture is lowered proceeding from 200 to 570° C. down to 100 to 200° C., and the isocyanate present in the reaction mixture is transferred wholly or partly to the injected liquid droplets as a result of condensation, while the phosgene and the hydrogen chloride remain essentially completely in the gas phase. Possible quench liquids mentioned are solvents, isocyanate mixtures and solvent/isocyanate mixtures. The injection of a quench liquid is mentioned for cooling of the reaction mixture and selective dissolution of the isocyanate formed in the solvent, with a first separation into a liquid phase and a gas phase comprising predominantly phosgene and hydrogen chloride as constituents. The two phases are then sent to an appropriate workup. There is no discussion of further desirable optimization options for this process step.

WO 2014/122180 A1 discloses a process for separating an isocyanate prepared by reacting a primary amine with an excess of phosgene in the gas phase from the gaseous crude product obtained in the reaction, in which the volume flow to the wash column is reduced by using an upstream heat exchanger or condenser, and hence one wash column of small diameter and having a small number of separation stages is adequate. Although it is possible to reduce the size of the wash column, there can be deposits in the condenser that require cleaning and hence a shutdown of the continuous process. Moreover, the installation of the condenser and the operation and maintenance thereof is associated with additional cost and inconvenience. According to the composition of the gaseous crude product, its corrosive properties have to be taken into account, which further increases cost and inconvenience or material demands for the condenser.

At low condensation temperatures, there is additionally an increased extent of unwanted condensation of phosgene out of the gas stream and hence an increase in the amount of phosgene present in the plant. This is undesirable for the purposes of efficient workup of the phosgene. For example, WO 2011/003532 A1 discusses the workup of the gas stream containing predominantly of phosgene and hydrogen chloride.

BRIEF DESCRIPTION OF THE FIGURES

The present invention will now be described for purposes of illustration and not limitation in conjunction with the figures, wherein.

DETAILED DESCRIPTION OF THE INVENTION

It was therefore an object of the present invention to provide a cleaning apparatus for separation of an organic isocyanate prepared by reacting an organic amine with a stoichiometric excess of phosgene in the gas phase from the gaseous crude product obtained in the reaction, with which the formation of deposits in the wash column and in apparatuses and pipelines present between the first separation unit (quench) and the wash column can be distinctly delayed and the condensation of phosgene out of the gas stream is very substantially avoided.

This object is achieved in accordance with the invention in that at least one addition unit (11) for direct introduction of at least one cooling fluid for an at least partial condensation and/or absorption of the gas stream conductable through the first gas conduit (9) is assigned to the first gas conduit (9). A reduction in the volume flow rate by condensation of the gaseous constituents is not necessarily the aim here. What is instead desired is that phosgene remains very substantially in the gas phase, in order to keep the amount of phosgene present in the plant to a minimum. According to the mode of operation, by virtue of the addition of the cooling fluid, there can even be a (slight) increase in the volume flow. What is crucial for the invention is instead prepurification of the gaseous product stream without necessarily affecting the volume flow.

The invention thus firstly provides a cleaning apparatus (1) for separating an organic isocyanate prepared by reacting an organic amine with a stoichiometric excess of phosgene in the gas phase from the gaseous crude product obtained in the reaction, comprising a first separating unit (2) having at least a crude product inlet (3) for a gaseous crude product stream containing at least the isocyanate, hydrogen chloride and unconverted phosgene, a first liquid inlet (4) for a liquid stream containing at least a quench liquid and a first liquid outlet (5) for a liquid stream containing at least some of the quench liquid and some of the isocyanate, wherein a first gas conduit (9) for conveying a gas stream containing at least hydrogen chloride, evaporated quench liquid and phosgene departs from the first separation unit (2), characterized in that at least one addition unit (11) for direct introduction of at least one cooling fluid for an at least partial condensation and/or absorption of the gas phase stream conductable through the first gas conduit (9) is assigned to the first gas conduit (9).

In the present context, cooling fluid is preferably understood to mean a liquid medium which is preferably free of compounds having Zerewitinoff-active groups that would react with isocyanate. Preferred cooling fluids are, for example, the quench liquids mentioned hereinafter. According to the preferred embodiment, the cooling fluid may also be removed at least partly from the process, for example as liquid from a second separation unit (10). Particular preference is given to a quench liquid which is also used to cool down the reaction mixture exiting from the reaction zone, where the isocyanate content in the cooling fluid is preferably ≤20% by weight, more preferably ≤10% by weight and most preferably ≤2% by weight.

In the present context, the gas stream which contains at least hydrogen chloride, evaporated quench liquid and phosgene and is conductable through the first gas conduit (9) is understood to mean a gas stream, which may also be an aerosol, containing a small proportion of liquid droplets and/or solid particles. Moreover, the gas stream may also contain even small amounts of isocyanate that have not yet been removed completely in the first separation unit (2). Even though there can be increased formation of liquid particularly downstream of the addition unit (11) essential to the invention and hence a gas phase and a liquid phase are present, this biphasic mixture conducted or conductable through the first gas conduit (9) is referred to hereinafter collectively as gas stream, since the liquid components have to some degree already passed from the first separation unit (2) into the first gas conduit (9) in gaseous form.

In the present context, "quench zone" is understood to mean a region in which the gaseous crude product is cooled down rapidly by injecting a quench liquid. In this quench zone, the reaction mixture consisting essentially of the isocyanate, phosgene and hydrogen chloride is mixed vigorously with the liquid injected. The mixing is effected in such a way that the temperature of the reaction mixture is lowered proceeding from 200 to 600° C. down to 100 to 200° C., and the isocyanate present in the reaction mixture is transferred wholly or partly to the injected liquid droplets as a result of condensation, while the phosgene and the hydrogen chloride remain essentially completely in the gas phase.

In the present context, the first separation unit (2) may be regarded as a quench zone. Thus, the first separation unit (2) is set up to rapidly cool and partly liquefy the gas stream conductable through the crude product inlet (3) by contacting with, preferably by injecting, a quench liquid ("quench"). Suitable first separation units (2) are described, for example, in EP 1 403 248 A1 (see especially the drawings with the corresponding elucidations in paragraphs [0017] to [0019]), and EP 1 935 875 A1 (see especially paragraphs [0015] to [0022] and [0033] to [0045]). For the conveying of the quench liquid, the separation unit (2) has a first liquid inlet (4).

Suitable quench liquids conductable through the first liquid inlet (4) are solvents, for example chlorobenzene, o-dichlorobenzene, p-dichlorobenzene, trichlorobenzenes, the corresponding chlorotoluenes or chloroxylenes, chloroethylbenzene, monochlorodiphenyl, α- or β-naphthyl chloride, ethyl benzoate, dialkyl phthalates, diisodiethyl phthalate, toluene and xylene, or mixtures thereof. Preferred solvents are chlorobenzene, o-dichlorobenzene and/or p-dichlorobenzene, and particular preference is given to chlorobenzene or o-dichlorobenzene. This additional stream of fresh, recycled and/or processed organic solvent preferably has a temperature of 40° C. to 150° C.

The first separation unit has a first liquid outlet (5) for a liquid stream containing at least some of the quench liquid and some of the isocyanate. In this context, a maximum proportion, preferably ≥80%, more preferably ≥90%, more preferably ≥98% and most preferably ≥99% to ≤99.95%, of the isocyanate present in the crude product stream is desirable. In the case of the aforementioned proportions, it should be noted that the vapor pressure of isocyanate sets a natural limit for the maximum separation of the isocyanate, and economic viability has to be weighed up against the benefit of approaching this limit as closely as possible. The gas stream obtained in this step may therefore generally still contain small amounts of isocyanate.

It is preferable that a first liquid conduit (6) for the return of a portion of the liquid stream conductable through the first liquid outlet (5) departs from the first liquid outlet (5) and opens into the first liquid inlet (4). If required, a pump (7) for forced conveying of this liquid stream may be assigned to the first liquid conduit (6). It is also possible that a quench cooler (8) for cooling of the liquid stream conductable through the second liquid conduit may be assigned to the first liquid conduit (6).

According to the invention, the terms "comprising" or "containing" preferably mean "consisting essentially of" and more preferably mean "consisting of".

The phosgenation of organic amines in the gas phase is known per se and can be effected, for example, as described in EP 0 289 840 B1, EP 1 319 655 A2, EP 1 555 258 A1, EP 1 275 639 A1, EP 1 275 640 A1, EP 1 449 826 A1, EP 1 754 698 B1, DE 10 359 627 A1 or DE 10 2005 042392 A1. Suitable organic amines are, for example, aniline, pentamethylenediamine (also PDA hereinafter), hexamethylenediamine (also HDA hereinafter), the isomers of isophoronediamine (also IPDA hereinafter), the isomers of xylylenediamine (also XDA hereinafter), the isomers of diaminodicyclohexylmethane (also H12-MDA hereinafter), the bicyclic isomers of methylenediphenyldiamine (also MDA hereinafter), and the isomers of tolylenediamine (also TDA hereinafter). Preference is given to TDA, PDA, HDA, IPDA and XDA, particular preference to TDA, PDA, HDA and IPDA, very particular preference to TDA and HDA.

The organic amine is reacted with phosgene in a continuous mode of operation. The reaction is preferably effected here at a temperature of 200° C. to 600° C., preferably of 300° C. to 500° C., and an absolute pressure of 150 mbar to 10 bar, preferably of 1.0 bar to 3.0 bar. The molar excess of phosgene is preferably 20% to 400% of theory. The gas stream obtained from the reaction of organic amine with phosgene contains at least the isocyanate, hydrogen chloride and unconverted phosgene and can be conducted through the crude product inlet (3) as crude product stream.

In a first preferred embodiment of the invention, the first removal unit (2) and/or the first gas conduit (9) is set up such that the gas stream conductable through the first gas conduit (9) is deflected at least once, preferably at least twice and more preferably 2 to 5 times before it reaches the addition unit (11). This has the advantage that a greater proportion of any entrained liquid droplets can be separated out. The deflections here can independently be effected in a vessel, wherein entry pipe and exit pipe are not disposed on opposite sides of the vessel, and/or by means of pipe bends incorporated in the first gas conduit (9). The first deflection can be effected here at an early stage, at the transition from the first separation unit (2) into the gas conduit (9).

In a further preferred embodiment of the invention, the addition unit (11) consists of one or more nozzles set up for direct introduction of the cooling fluid in cocurrent or countercurrent, preferably in cocurrent, or, likewise preferably, consists of multiple nozzles positioned in the conduit shell of the first gas conduit (9), more preferably at uniform intervals along the circumference of the first gas conduit (9). This results in the advantage that a fine mist is generated, which leads to further-improved agglomeration of the aerosol particles.

More preferably, the one or more nozzles are arranged such that the mist generated covers the entire pipe cross section. Suitable nozzles are known from the prior art. It is possible to use, for example, simple perforated nozzles, but also those having internals or two-phase nozzles. Preference is given to one-phase nozzles in order to avoid additional gas loading on the apparatuses downstream.

In a very particularly preferred embodiment of the invention, the addition unit (11) is in a vertical pipeline section in which the gaseous crude product flows from the top downward.

In a further embodiment, it is also possible for two or more such addition units (11) to be arranged successively in flow direction of the gas.

As an alternative to the aforementioned preferred embodiment, it is also preferable when the addition unit (11) has at least one orifice and preferably two or more orifices for generation of a fluid curtain over the entire cross section of the first gas conduit (9), positioned in a horizontal pipeline section in the upper region of the conduit shell of the first gas conduit (9), such that the gas flow crosses the lamellae or jets of the fluid curtain. It is possible here that the orifices have a round or slot-shaped configuration, or that they are flat-jet nozzles for example. Also possible is the guiding of the fluid curtain through a coalescence aid mounted in the pipeline. Horizontal pipeline sections in the context of the invention are considered to be those pipe conduits having a gradient of less than 60%, preferably a gradient of less than 10%, more preferably a gradient of 0.01-2%. This results in the advantage that the probability of agglomeration of the aerosol particles is also increased further in this way.

Of the two aforementioned alternative preferred embodiments, the first embodiment is particularly preferred since this can be particularly effective under some circumstances.

In a further preferred embodiment, the addition unit (11) has a cooling fluid inlet (12) for conveying the cooling fluid.

In a development of the invention, it is envisaged that the first gas conduit (9) leads to a second separation unit (10).

It is further preferable here that a second liquid conduit (13) for at least partial recycling of a liquid stream as quench liquid departs from the second separation unit (10) and leads to the first separation unit (2). If required, this liquid stream can be forcibly conveyed, for example by means of a pump (14).

The cooling fluid inlet (12) may, inter alia, originate directly from a reservoir vessel for the cooling fluid. It preferably originates as a branch from the second liquid conduit (13), such that both conduits ((12) and (13)) can be supplied by means of a common pump (14).

It is particularly preferable here that closed-loop control devices (15a) and (15b) for control of the liquid flow rates conductable through the second liquid conduit (13) to the first separation unit (2) on the one hand and through the cooling fluid inlet (12) to the addition unit (11) on the other hand are additionally assigned to the second liquid conduit (13) and to the cooling fluid inlet (12). Such closed-loop control devices are sufficiently well known from the prior art. They may be simple manual fittings by means of which a limitation of the free conduit cross section can be established and hence the volume flow can be limited. Preference is given to using a combination of sensor and actuator that regulates the respective flow rates in a self-contained manner to a defined value by means of automated closed-loop control. Sensors used may, for example, be volume flowmeters such as magnetic induction flowmeters, variable area flowmeters, ultrasound flowmeters, measuring orifices, Pitot tubes or mass flowmeters such as Coriolis mass flowmeters, thermal mass flowmeters or vortex mass flowmeters. Actuators used are, for example, motor-driven gate valves, rotary ball valves, ballcocks, piston valves or shutoff valves. This results in the advantage that the temperatures in the first separation unit (2) and in the addition unit (11) can be controlled via the amount of cooling fluid, and that the amount of additional cooling fluid can be adjusted to an optimally low level such that sufficient prepurification is achieved but the cost and inconvenience associated with processing or procurement of the additional cooling fluid is minimized.

In order to obtain an additional degree of freedom in the adjustment of the suitable operating parameters, a heat exchanger (16) to control the temperature of the liquid streams conductable through the conduits can be assigned to the cooling fluid inlet (12) and/or the second liquid conduit (13). Suitable heat exchangers and their mode of operation are known to the person skilled in the art from the prior art; it is possible, inter alia, to use shell and tube heat exchangers or plate heat exchangers.

The second separation unit (10) may have a fourth liquid conduit (21) for addition of a liquid stream. The second separation unit (10) preferably has a second gas conduit (17) for discharge of the uncondensed gas stream, which more preferably departs in the upper portion of the second separation unit (10). A condenser (18) for at least partial condensation of the gas stream conductable through the second gas conduit (17) is assigned to the second gas conduit (17). In addition, the condenser (18) has a third liquid conduit (20) for recycling of the condensed liquid stream, which opens into the second separation unit (10).

In a further embodiment, any liquid obtained in the gas stream conductable through the first gas conduit (9) can be drained into the lower portion of the first removal unit (2), but it is preferable that the first gas conduit (9) runs with a gradient from the addition unit (11) to the second separation unit (10), such that gravity offers sufficient driving force to convey liquid obtained to the second separation unit (10) and in this way to avoid accumulations of liquid in the region of the addition unit (11).

The second separation unit (10) is preferably a wash column with at least one separation stage, where the wash column can be supplied with at least one solvent stream as wash liquid. Suitable wash columns (10) are described, for example, in Perry's Chemical Engineers' Handbook, 7th Edition, McGraw-Hill, chapter 14 "Gas Absorption and Gas-Liquid System Design". Preferably, the liquid stream conductable through the third liquid conduit (20) and/or through the fourth liquid conduit (21) contains chlorinated aromatic hydrocarbons, for example chlorobenzene, o-dichlorobenzene, p-dichlorobenzene, trichlorobenzenes, the corresponding chlorotoluenes or chloroxylenes, chloroethylbenzene, monochlorodiphenyl, α- or β-naphthyl chloride, ethyl benzoate, dialkyl phthalates, diisodiethyl phthalate, toluene and xylene. Particularly preferred solvents are chlorobenzene and the isomers of dichlorobenzenes; very particular preference is given to chlorobenzene or o-dichlorobenzene. The at least one solvent stream may consist of fresh solvent. However, it is also possible to use recycled, optionally reprocessed solvent-containing streams or mixtures of the aforementioned solvents.

In a further preferred embodiment, the fourth conduit (21) is disposed above the separation stage in the wash column (10), and in the case of presence of multiple separation stages above the uppermost separation stage. When the solvent stream that is to be used is not fresh solvent but a recycled solvent-containing stream, it should be ensured that this is essentially free of the organic isocyanate to be removed, and preferably contains the organic isocyanate to be removed in a proportion by mass of not more than 100 ppm, based on the total mass of the liquid stream conductable through the fourth liquid conduit (21), in order to avoid the formation of breakdown products.

As an alternative to or in combination with this embodiment, the second separation unit (10), preferably the wash column (10), may have a fifth liquid conduit (22) for addition of a liquid stream which is fed in below the separation stage, and in the case of presence of multiple separation stages below the lowermost separation stage. It may be incorporated into the separation unit itself (shown in schematic form by way of example in FIG. 2 as the fifth liquid conduit (22A)) and/or into the corresponding drainpipe for liquids (13) (shown in schematic form by way of example in FIG. 2 as the fifth liquid conduit (22B)), and in the case of use of a forced conveyor preferably on the suction side thereof, i.e. into the second separation unit and/or between the second separation unit and forced conveyor. This embodiment offers the advantage of improved mixing of the liquid streams. When the liquid stream conductable through the fifth liquid conduit (22) is not fresh solvent but a recycled solvent-containing stream, the demands here on the maximum isocyanate content are less strict than in the case of the liquid stream conductable through the fourth liquid conduit (21). Owing to the direct contribution of the latter stream to the vapor/liquid equilibrium with the vaporous top product stream from the wash column, which must be largely isocyanate-free, only very much smaller isocyanate contents can be allowed in this liquid stream than in the stream conductable through the fifth liquid conduit (22). Therefore, the liquid stream conductable through the fifth liquid conduit (22) may contain up to 20% by weight of isocyanate, preferably up to 10% by weight of isocyanate and more preferably up to 2% by weight of isocyanate, based on the total mass of the liquid stream conductable through the fifth liquid conduit (22).

The condenser (18) has a third gas conduit (19) for conveying the uncondensed gas stream. This uncondensed gas stream consists essentially of hydrogen chloride gas, phosgene, further gases, for example nitrogen and carbon monoxide, and small amounts of solvent, and is preferably sent to a further workup, where solvent, excess phosgene and hydrogen chloride gas formed are generally separated from one another. For economic reasons, solvent and excess phosgene are preferably sent (separately) back to the reaction. The hydrogen chloride can be sent to various possible uses, for example an oxychlorination of ethylene to ethylene dichloride or a recycling process that recycles chlorine back into the isocyanate process. These recycling processes include the catalytic oxidation of hydrogen chloride, for example by the deacon process, the electrolysis of gaseous hydrogen chloride and the electrolysis of an aqueous solution of hydrogen chloride (hydrochloric acid).

The operation of the addition unit (11) in the process of the invention allows the service life before cleaning and hence an interruption in continuous operation is required to be considerably extended compared to the prior art. This is achieved since, under otherwise identical pressure and temperature conditions in the inlet to the second removal unit (10), there is already more significant enrichment of entrained organic impurities in the liquid phase of the gas stream conductable through the first gas conduit (9).

The advantages of the present invention cannot be achieved by simple reduction in the condensation temperatures in the known prior art condenser since deposits rapidly arise on the very cold surfaces of the condenser, as a result of which it is either no longer possible to maintain the temperature or the condenser even becomes blocked and has to be cleaned and hence the maintenance intensity would be increased. Furthermore, in the case of operation of a condenser at lower temperatures as described in WO 2014/122180 A1, for example, there is unwanted condensation of phosgene out of the gas stream and hence a distinct increase in the amount of phosgene present in the plant. It is immaterial here whether the condenser is irrigated or not. What is desirable at this point is for the phosgene to remain predominantly in the gas phase, such that it can subsequently be purified further as described in WO 2011/003532 A1 and recycled into the process. Preferably, downstream of the addition unit (11), ≥90% of the phosgene is in the gas phase of the gas stream, more preferably ≥95% and most preferably >97% to ≤99.5%.

By virtue of the addition unit (11) which is essential to the invention, in operation of the cleaning apparatus (1), it is possible to achieve improved removal of any liquid and/or solid particles present in the gas stream conductable through the first gas conduit (9). Therefore, the present invention further provides a process for separating an organic isocyanate prepared by reacting an organic amine with a stoichiometric excess of phosgene in the gas phase from the gaseous crude product obtained in the reaction, comprising the steps of
(i) at least partial condensation of the crude product stream containing at least the isocyanate, hydrogen chloride and unconverted phosgene by contacting with at least one liquid stream containing at least one quench liquid in a first separation apparatus (2) to obtain
a liquid stream containing at least some of the quench liquid and some of the isocyanate and
a gas stream containing at least hydrogen chloride, evaporated quench liquid and phosgene,
(ii) discharge of the liquid stream obtained in step (i) via a first liquid outlet (5) and of the gas stream obtained in (i) via a first gas conduit (9) and
(iii) at least partial condensation and/or absorption of the gas stream discharged in step (ii) through the first gas conduit (9),
characterized in that the at least partial condensation and/or absorption is effected in step (iii) by direct introduction of at least one cooling fluid, wherein the cooling fluid is introduced directly into the first gas conduit (9) via at least one addition unit (11) assigned to the first gas conduit (9).

In a first preferred embodiment of the process of the invention, the weight ratio of the cooling fluid introduced to the gas stream conducted through the first gas conduit (9) is preferably 1:100 to 10:1, more preferably 1:12 to 1:1, most preferably 1:10 to 1:2. Downstream of the addition of the cooling fluid, via regulation of the weight ratio and optionally the cooling fluid temperature, a temperature below that of the gas stream obtained in step (i) is established. At a pressure of 1.5 bar(a), the temperature is preferably between 100° C. and 170° C., more preferably between 110° C. and 150° C. and most preferably between 110 and 128° C. This prevents too much phosgene from going into the liquid phase and hence an increase in the amount of phosgene present in the plant. At higher or lower pressure and depending on the cooling fluid use or quench fluid used, the preferred temperatures may be higher or lower in accordance with the rules of thermodynamics. As a further preferred embodiment, the process of the invention is conducted in such a way that the addition unit (11) establishes a lowering of the temperature in the gas stream by 0.5 to 50 K, preferably by 1 to 40 K and more preferably by 3 to 30 K.

In a further preferred embodiment of the process of the invention, the cooling fluid has a temperature of ≥40 bis ≤130° C., preferably of ≥60 to ≤120° C. and more preferably of ≥80 to ≤110° C. This temperature range leads to an effective reduction in deposits and prevents excessive washing of phosgene out of the gas stream. In a further preferred embodiment, the cooling fluid is selected to correspond to the solvent used as quench liquid in step (i).

In a further preferred embodiment, the process of the invention comprises the further steps of:
(iv) separating the gas stream from the first gas conduit (9) in a second separation unit (10) into a liquid stream and a gas stream and
(v) recycling the liquid stream obtained in step (iv) as quench liquid via a second liquid conduit (13) into the first separation unit (2), it being possible and preferable to branch off a substream as cooling fluid into the cooling fluid inlet (12).

It is particularly preferable here when the liquid stream recycled into step (v) is taken from the bottoms from the second separation unit (10). Thus, in a particularly economically viable manner, the isocyanate washed out in the second separation unit is combined with the crude product in the first separation unit (2) and then they are worked up together with the isocyanate present therein. By means of the optionally used heat exchanger (16), it is possible to adjust the temperature of liquid streams recycled into step (v), which offers an additional degree of freedom in the establishment of the suitable operating parameters.

In a further preferred embodiment of the process of the invention, the cooling fluid is chlorobenzene, o-dichlorobenzene, p-dichlorobenzene, trichlorobenzenes, the corresponding chlorotoluenes or chloroxylenes, chloroethylbenzene, monochlorodiphenyl, α- or β-naphthyl chloride, ethyl benzoate, dialkyl phthalates, diisodiethyl phthalate, toluene and/or xylene, preferably chlorobenzene, o-dichlorobenzene and/or p-dichlorobenzene and more preferably chlorobenzene or o-dichlorobenzene.

The direct addition of a cooling fluid to a gas stream from the quench zone in the preparation of organic isocyanates leads to lower formation of deposits and therefore allows prolonged continuous operation before this has to be interrupted for cleaning purposes, which has a direct positive effect on space-time yield. Thus, the present invention further provides for the use of a cooling fluid for optimization of the phosgene to isocyanate mass ratio of a gas stream from the first separation unit (2), preferably from the quench zone, in an isocyanate preparation by direct addition of the cooling fluid to a first gas conduit (9) that conducts said gas stream. In this case, the first separation unit (2) has at least one crude product inlet (3) for a gaseous crude product stream containing at least the isocyanate, hydrogen chloride and unconverted phosgene, a first liquid inlet (4) for a liquid stream containing at least one quench liquid and a first liquid outlet (5) for a liquid stream containing at least a portion of the quench liquid and a portion of the isocyanate, and a first gas conduit (9) for discharge of a gas stream containing at least hydrogen chloride, evaporated quench liquid and phosgene. In the case of this use, preference is given to using the aforementioned cooling fluids, quench liquids and/or solvents.

By virtue of the addition unit (11) being used in the cleaning apparatus (1) of the invention and/or in the process of the invention and/or in the case of use of the cooling fluid in accordance with the invention, the treated gas stream has particular properties that simplify subsequent treatment.

The present invention therefore further provides a gas stream for treatment in at least one second separation unit (10), preferably in at least one wash column (10), wherein the gas stream on entry into the second separation unit (10) includes phosgene and isocyanate in a mass ratio of ≥1:1 to ≤10 000:1, preferably of ≥1:1 to ≤5000:1 and more preferably of ≥1:1 to ≤1000:1. In this context, the aforementioned general and preferred configurations are likewise applicable to the second separation unit (10), preferably the wash column (10). The gas stream preferably corresponds to the gas stream conductable through the first gas conduit (9). If the gas stream, irrespective of its origin, should contain liquid fractions, the aforementioned mass ratios are based on the contents in the gas phase.

Figure 1:
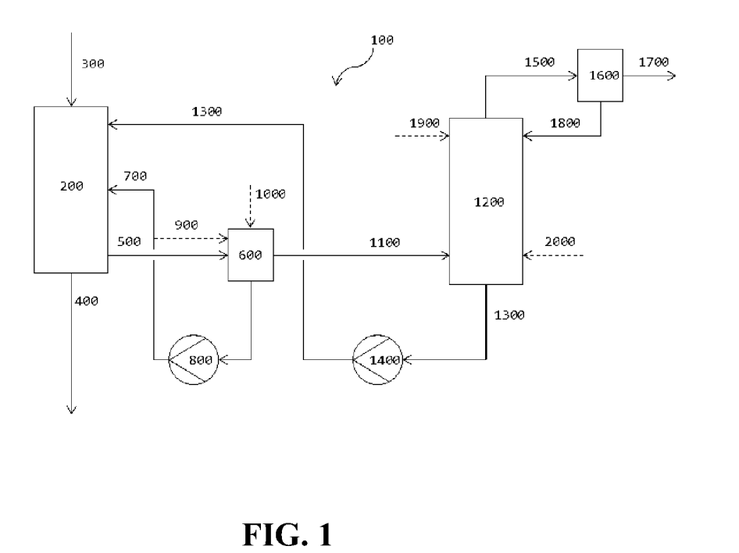
FIG. 1 shows a schematic of the cleaning apparatus known from FIG. 2 of WO 2014/122180 A1.

The present invention is elucidated in detail with reference to the figures and examples which follow, but without being restricted thereto. The figures show:

FIG. 1 shows a schematic of an embodiment of a cleaning apparatus (100) known from WO 2014/122180 A1 for separating an organic isocyanate prepared by reacting an organic amine with a stoichiometric excess of phosgene in the gas phase from the gaseous crude product obtained in the reaction.

The cleaning apparatus (100) consists of a first separation unit (200) having a crude product inlet (300) for a gaseous crude product stream containing at least the isocyanate, hydrogen chloride and unconverted phosgene. In addition, the first separation unit (200) has a first liquid outlet (400) for the discharge of a liquid stream containing at least some of the quench liquid and some of the isocyanate.

Also departing from the first separation unit (200) is a first gas conduit (500) for conveying a gas stream containing at least hydrogen chloride, evaporated quench liquid and phosgene, and this ends in a first condenser (600). This condenser is set up such that at least some of the gas stream conductable through the first gas conduit (500) is condensed. A first liquid conduit (700) for conveying the condensed liquid departs from the condenser (600).

The liquid conduit (700) ends in the first separation unit (200). Assigned to the liquid conduit (700) is a pump (800) for forced conveying of the liquid conductable through the liquid conduit (700). The condenser (600) may additionally have a second liquid conduit (900) for feeding in a portion of the liquid stream conductable through the first liquid conduit (700) and/or a third liquid conduit (1000) for feeding in a solvent stream. A second gas conduit (1100) for conveying the gaseous uncondensed fraction departs from the condenser and ends in a second separation unit (1200).

A fourth liquid conduit (1300) for the recycling of a liquid stream as quench liquid departs from the second separation unit (1200) and ends in the first separation unit (200). Assigned to the fourth liquid conduit (1300) is a pump (1400) for forced conveying of the liquid stream conductable through the fourth liquid conduit (1300).

The second separation unit (1200) has a third gas conduit (1500) for discharge of an uncondensed gas stream. A second condenser (1600) for at least partial condensation of the gas stream conductable through the third gas conduit (1500) is assigned to the third gas conduit (1500). The second condenser (1600) has a fourth gas conduit (1700) for discharge of the uncondensed gas stream. In addition, the second condenser (1600) has a fifth liquid conduit (1800) for recycling of the condensed liquid stream, which opens into the second separation unit (1200).

The second separation unit (1200) may additionally have a sixth liquid conduit (1900) for addition of a liquid stream, disposed in the upper portion of the second separation unit (1200). Additionally or alternatively, the second separation unit (1200) may have a seventh liquid conduit (2000) for addition of a further liquid stream, disposed in the lower portion of the second separation unit (1200).

In operation of the cleaning apparatus (100) described in FIG. 1, for separation of an organic isocyanate prepared by reacting an organic amine with a stoichiometric excess of phosgene in the gas phase from the gaseous crude product obtained in the reaction, a gaseous crude product stream containing at least the isocyanate, hydrogen chloride and unconverted phosgene is first conducted through the crude product inlet (300) into the first separation unit (200).

In the first separation unit (200), this crude product stream is partly condensed by adding a liquid stream containing at least one quench liquid via the first liquid conduit (700). A liquid stream containing at least some of the quench liquid and some of the isocyanate leaves the first separation unit (200) via the first liquid outlet (400).

In addition, a gas stream containing at least hydrogen chloride, evaporated quench liquid and phosgene leaves the first separation unit (200) via the first gas conduit (500) toward the first condenser (600). This gas stream is at least partly condensed in the condenser (600). The liquid obtained is recycled into the first separation unit (200) through the first liquid conduit (700) with forcible conveying by means of the pump (800).

Some of the liquid conducted through the first liquid conduit (700) can be branched off into the second liquid conduit (900) and hence fed back to the condenser (600). Alternatively or additionally, further solvent can be fed in through the third liquid conduit (1000). The uncondensed fraction in gaseous form in the condenser (600) is conveyed through the second gas conduit (1100) into the second separation unit (1200).

The liquid present in the second separation unit (1200) is recycled as quench liquid into the first separation unit (200) via the fourth liquid conduit (1300). This recycling is effected with forcible conveying by the pump (1400). The gas stream uncondensed in the second separation unit (1200) is discharged via the third gas conduit (1500) and at least partly condensed in the second condenser (1600). The fraction uncondensed here is discharged from the condenser (1600) via the fourth gas conduit (1700). The liquefied fraction is recycled via the liquid conduit (1800) into the second separation unit (1200).

An additional liquid stream can be supplied to the second separation unit (1200) via the optional sixth liquid conduit (1900) disposed in the upper portion of the second separation unit (1200). A further liquid stream can be supplied to the second separation unit (1200) via the optional seventh liquid conduit (2000) disposed in the lower portion of the second separation unit (1200).

Figure 2:
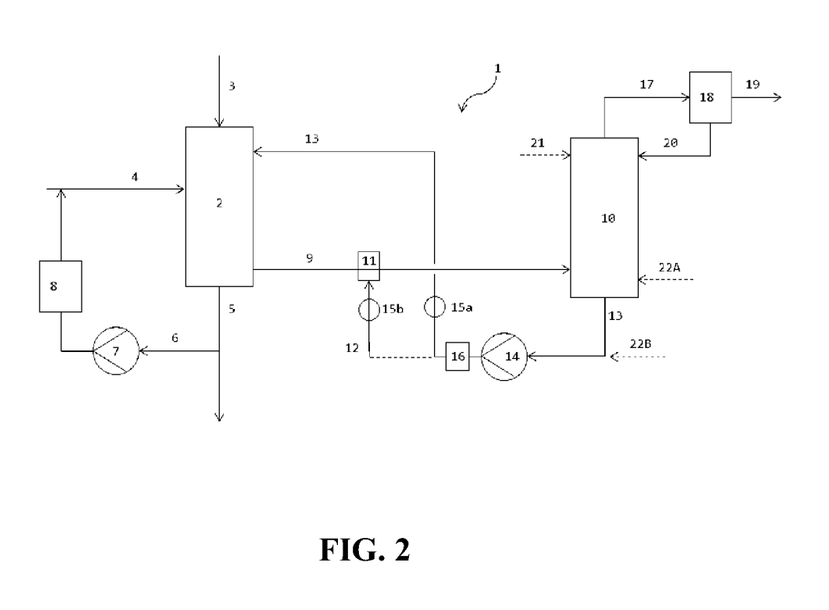
FIG. 2 shows a schematic of an embodiment of the cleaning apparatus of the invention.

FIG. 2 shows a schematic embodiment of the cleaning apparatus (1) of the invention for separating an organic isocyanate prepared by reacting an organic amine with a stoichiometric excess of phosgene in the gas phase from the gaseous crude product obtained in the reaction.

The cleaning apparatus (1) consists of a first separation unit (2) having a crude product inlet (3) for a gaseous crude product stream containing at least the isocyanate, hydrogen chloride and unconverted phosgene. A first liquid inlet (4) for a liquid stream containing at least a quench liquid opens into the separation unit (2). In addition, the first separation unit (2) has a first liquid outlet (5) for a liquid stream containing at least some of the quench liquid and some of the isocyanate. A first liquid conduit (6) for the return of a portion of the liquid stream conductable through the first liquid outlet (5) departs from the first liquid outlet (5) and opens into the first liquid inlet (4). Assigned to the first liquid conduit (6) is a pump (7) for forced conveying of this liquid stream and a quench cooler (8) for cooling of the liquid stream conductable through the first liquid conduit.

Also departing from the first separation unit (2) is a first gas conduit (9) for conveying a gas stream containing at least hydrogen chloride, evaporated quench liquid and phosgene, and this leads to a second separation unit (10). To the first gas conduit (9) is assigned an addition unit (11) for direct introduction of at least one cooling fluid. The addition unit (11) has a cooling fluid inlet (12) for conveying the cooling fluid.

A second liquid conduit (13) for the partial recycling of a liquid stream as quench liquid departs from the second separation unit (10) and ends in the first separation unit (2). The cooling fluid inlet (12) may, inter alia, originate directly from a reservoir vessel for the cooling fluid. It preferably originates as a branch from the second liquid conduit (13), such that both conduits (12 and 13) can be supplied by means of a pump (14) assigned to the second liquid conduit (13). Closed-loop control devices (15a) and (15b) for control of the liquid flow rates through the second liquid conduit (13) to the first separation unit (2) on the one hand and through the cooling fluid inlet (12) to the addition unit (11) on the other hand are also assigned to the second liquid conduit (13) and to the cooling fluid inlet (12). Downstream of the pump (14), a heat exchanger (16) for regulation of the temperature of the liquid stream conductable through the second liquid conduit (13) is additionally assigned to the second liquid conduit (13).

The second separation unit (10) has a second gas conduit (17) for discharge of an uncondensed gas stream. A condenser (18) for at least partial condensation of the gas stream conductable through second gas conduit (17) is assigned to the second gas conduit (17). The condenser (18) has a third gas conduit (19) for discharging the uncondensed gas stream. In addition, the condenser (18) has a third liquid conduit (20) for recycling of the condensed liquid stream, which opens into the second separation unit (10).

The second separation unit (10) additionally has a fourth liquid conduit (21) for addition of a liquid stream, disposed in the upper portion of the second separation unit (10). In addition, the second separation unit (10) may have a fifth liquid conduit (22A) for addition of a further liquid stream, disposed in the lower portion of the second separation unit (10). Alternatively, this fifth liquid conduit (22A) may open into the second liquid conduit (13) as fifth liquid conduit (22B).

In operation of the cleaning apparatus (1) described in FIG. 2, for separation of an organic isocyanate prepared by reacting an organic amine with a stoichiometric excess of phosgene in the gas phase from the gaseous crude product obtained in the reaction, a gaseous crude product stream containing at least the isocyanate, hydrogen chloride and unconverted phosgene is first conducted through the crude product inlet (3) into the first separation unit (2).

In the first separation unit (2), this crude product stream is partly condensed by adding a liquid stream containing at least one quench liquid via the first liquid inlet (4). A liquid stream containing at least some of the quench liquid and some of the isocyanate leaves the first separation unit (2) via the first liquid outlet (5). A portion of this liquid stream is forcibly conveyed through the first liquid conduit (6) by means of the pump (7) and, having been cooled by means of the quench cooler (8), recycled into the first liquid inlet (4) and hence reused as quench liquid.

In addition, a gas stream containing at least hydrogen chloride, evaporated quench liquid and phosgene leaves the separation unit (2) via the first gas conduit (9) to the second separation unit (10). A cooling fluid inert toward isocyanate groups is introduced directly into the first gas conduit (9) via the addition unit (11), as a result of which the gas stream is at least partly condensed and/or absorbed. The cooling fluid is conveyed through the cooling fluid inlet (12) to the addition unit (11).

The partly condensed and/or absorbed gas stream from the first gas conduit (9) is subjected to further treatment in the second separation unit (10). This treatment affords a liquid stream which is recycled at least partly via the second liquid conduit (13) as quench liquid to the first separation unit (2). The recycling is effected with forcible conveying via the pump (14) assigned to the second liquid conduit (13). The cooling fluid inlet (12) may, inter alia, originate directly from a reservoir vessel for the cooling fluid. It preferably originates as a branch from the second liquid conduit (13), such that both conduits (12 and 13) are supplied by means of the pump (14).

The liquid flow rates through the second liquid conduit (13) to the first separation unit (2) on the one hand and through the cooling fluid inlet (12) to the addition unit (11) on the other hand are controlled by the closed-loop control units (15a) and (15b). The temperature of the liquid streams is controlled by the heat exchanger (16).

The fraction uncondensed in the second separation unit (10) is discharged via the second gas conduit (17) and at least partly condensed by means of the condenser (18) assigned to the second gas conduit (17). The fraction that remains in gaseous form here is discharged from the condenser via the third gas conduit (19) as uncondensed gas stream. The liquefied fraction is recycled from the condenser (18) into the second separation unit (10) via the third liquid conduit (20). If required, additional liquid can be added to the second separation unit (10) via the fourth liquid conduit (21) and/or the fifth liquid conduit (22A) or (22B).

The views of FIGS. 3, 3A, 3B, 3C, and 3D show a schematic of various embodiments of the addition unit (11).

Figure 3:
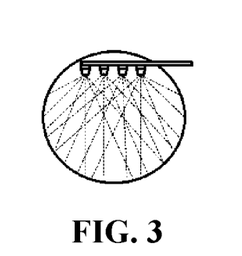
FIG. 3 shows a cross section through the first gas conduit, wherein the cooling fluid is introduced into the gas conduit via a bar equipped with nozzles on its underside.

For instance, FIG. 3 shows a cross section through the first gas conduit (9), wherein the cooling fluid is introduced into the gas conduit via a bar equipped with nozzles on its underside.

Figure 3A:
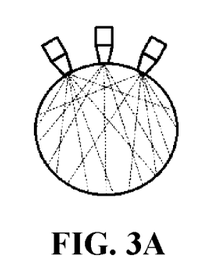
FIG. 3A shows an arrangement of FIG. 3 in which the nozzles are integrated into the wall of the first gas conduit.

FIG. 3A shows an arrangement in which the nozzles are integrated into the wall of the first gas conduit (9).

Figure 3B:
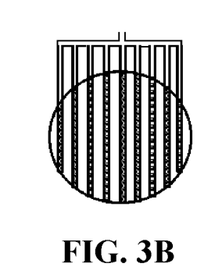
FIG. 3B shows a variant of FIG. 3 of the addition unit without the use of nozzles.

FIG. 3B shows a variant of the addition unit without the use of nozzles. The cooling fluid is added here through simple holes in the upper region of the wall of the first gas conduit (9). A lamellar curtain is formed, which crosses the mixture flowing through the gas conduit.

Figure 3C:
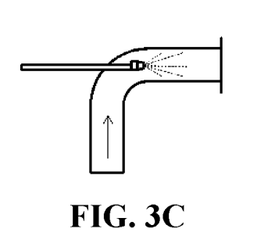
FIG. 3C shows a further variant of the addition unit.

FIG. 3C shows a further variant of the addition unit. This is a longitudinal section through the first gas conduit (9), wherein the cooling fluid is added via a bar with a nozzle at its end for fine spraying of the cooling fluid. The gas conduit here contains a 90° pipe bend and the bar is arranged such that the nozzle is downstream of the pipe bend and the cooling fluid is sprayed in cocurrent with the substance mixture that flows through the gas conduit.

FIG. 3D again shows an arrangement in cross section in which the nozzles are integrated into the wall of the first gas conduit (9), this time distributed uniformly over the pipe circumference and not all in the upper half of the pipe cross section as in FIG. 3A.

EXAMPLES

Example 1 (Comparative Example)

In a pilot plant for preparation of hexamethylene diisocyanate in the gas phase, a first separation unit in which the crude product was cooled down by means of addition of chlorobenzene was connected downstream of the reaction zone. This condensed 99% of the isocyanate and separated it off as liquid crude product dissolved in chlorobenzene. The uncondensed fraction of the crude product leaving the reaction zone was cooled by a further 10 K to 120° C. in a shell and tube heat exchanger. The heat exchanger here was irrigated here with just sufficient chlorobenzene to uniformly wet its heat transfer surfaces, in order to avoid caking. The gas stream was on the tube side of the condenser, and the heat was removed via a cooling water stream on the shell side of the condenser. To control the temperature, it was possible to throttle the cooling water stream by means of a ball valve. In addition, the entrance and exit temperature on the gas side was measured continuously over the duration of the experiment. Later on, the crude product stream that had been cooled down in this way was guided into a wash column, at the top of which a stream of chlorobenzene and phosgene was removed, while organic impurities were concentrated at the bottom and discharged as a liquid stream. In this wash column, the pressure differential between the gas space below the lowermost separation stage and the gas space above the uppermost separation stage was measured continuously.

In thermodynamic model calculations (ASPEN PLUS V7.2), it was shown that about 0.1% of the phosgene that enters the condenser was precipitated as liquid in the condenser. For this purpose, a gaseous stream consisting of 20% by weight of phosgene, 15% by weight of HCl and 65% by weight of chlorobenzene at 1.5 bar(a) was cooled down from 130° C. to 120° C. in a "Flash2", and the distribution of the phosgene between the liquid and gaseous output stream of the flash was examined.

Within about 12 days of continuous operation, the pressure drop in the wash column rose from originally 102 mbar to an impermissibly high value of 150 mbar.

Example 2 (Comparative Example)

The same arrangement as in example 1 was employed. This time, however, the exit temperature of the condenser on the process side was set to 50° C. Although it was possible to operate the wash column with this condensation temperature for a significantly longer period than in example 1, there was significant enrichment of phosgene in the condensate obtained.

In thermodynamic model calculations (ASPEN PLUS V7.2), it was shown that about 20% of the phosgene that enters the condenser was precipitated as liquid in the condenser. For this purpose, a gaseous stream consisting of 20% by weight of phosgene, 15% by weight of HCl and 65% by weight of chlorobenzene at 1.5 bar(a) was cooled down from 130° C. to 50° C. in a "Flash2", and the distribution of the phosgene between the liquid and gaseous output stream of the flash was examined.

Example 3 (Inventive)

Figure 3D:
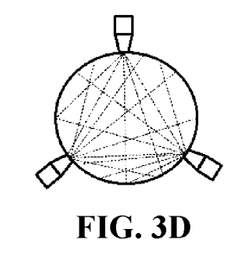
FIG. 3D shows an arrangement of FIG. 3 in cross section in which the nozzles are integrated into the wall of the first gas conduit.

The arrangement for example 1 was modified in that the shell and tube heat exchanger together with the first liquid outlet was replaced by a simple pipe section equipped with an addition unit for chlorobenzene. This was a simple one-phase nozzle which, as indicated in FIG. 3D, was in the middle of the pipeline and by means of which the chlorobenzene could be sprayed centrally into the pipeline in cocurrent. The pressure in the chlorobenzene feed to the nozzle was adjusted such that the pressure drop on exit from the nozzle led to fine atomization of the liquid. The nozzle generated a full cone with opening angle 45° in cocurrent with the gas stream. The mass flow of chlorobenzene to the addition unit was chosen such that the ratio of this and the mass flow of uncondensed crude product to the addition unit was 1:7; the temperature of the chlorobenzene in the feed to the addition unit was 95° C.; the gas stream had a temperature of 130° C. upstream of the addition unit. Downstream of the addition unit, a temperature of 122° C. was established. After 27 days, the experiment was stopped. The pressure drop over the addition unit and over the wash column was constant within this period. Even in the subsequent inspection of the apparatuses, there were no signs of deposits.

In thermodynamic model calculations (ASPEN PLUS V7.2), it was shown that about 0.5% of the phosgene conducted through the gas conduit was precipitated in the liquid. For this purpose, a gaseous stream at 130° C. consisting of 20% by weight of phosgene, 15% by weight of HCl and 65% by weight of chlorobenzene was mixed with a liquid chlorobenzene stream at 95° C. in a mixer. Analogously to the experiment, the weight ratio was set to 1:7 (chlorobenzene:gas stream). The mixed stream was then separated into a gaseous stream and a liquid stream at 1.5 bar(a) in a "Flash2" without further supply or removal of heat, and the distribution of the phosgene between these two streams was examined.

Example 4 (Inventive)

In a pilot plant for preparation of isophorone diisocyanate in the gas phase, a first separation unit in which the crude product was cooled down by means of addition of chlorobenzene was connected downstream of the reaction zone. This condensed 99.2% of the isocyanate and separated it off as liquid crude product dissolved in chlorobenzene. The uncondensed fraction of the crude product leaving the reaction zone had a temperature of 145° C. and was discharged from the gas-liquid separator by means of a pipeline. In this pipeline, there was an addition unit for chlorobenzene corresponding to the arrangement in example 3. In a departure from example 3, the mass flow of chlorobenzene to the addition unit was this time chosen such that the ratio of this and the mass flow of uncondensed crude product to the addition unit was 1:3. Downstream of the addition unit, a temperature of 122° C. was established. After 25 days, the experiment was stopped. The pressure drop over the addition unit and over the wash column was constant within this period. Even in the subsequent inspection of the apparatuses, there were no signs of deposits.

In thermodynamic model calculations (ASPEN PLUS V7.2), it was shown that about 1% of the phosgene conducted through the gas conduit was precipitated in the liquid. For this purpose, a gaseous stream at 145° C. consisting of 20% by weight of phosgene, 15% by weight of HCl and 65% by weight of chlorobenzene was mixed with a liquid chlorobenzene stream at 95° C. in a mixer. Analogously to the experiment, the weight ratio was set to 1:3 (chlorobenzene:gas stream). The mixed stream was then separated into a gaseous stream and a liquid stream at 1.5 bar(a) in a "Flash2" without further supply or removal of heat, and the distribution of the phosgene between these two streams was examined.

Example 5 (Inventive)

In a pilot plant for preparation of tolylene diisocyanate in the gas phase, a first separation unit in which the crude product was cooled down by means of addition of o-dichlorobenzene was connected downstream of the reaction zone. This condensed 98.5% of the isocyanate and separated it off as liquid crude product dissolved in o-dichlorobenzene. The uncondensed fraction of the crude product leaving the reaction zone had a temperature of 170° C. and was discharged from the gas-liquid separator by means of a pipeline. In this pipeline, there was an addition unit for cooling fluid. Unlike in example 3, the cooling fluid this time was withdrawn at the bottom of the second separation unit and heated to 85° C. by means of a shell and tube heat exchanger. The mass flow of the cooling fluid was chosen such that the ratio of this and the mass flow of uncondensed crude product to the addition unit was 1:2. Downstream of the addition unit, a temperature of 157° C. was established. After 22 days, the experiment was stopped. The pressure drop over the addition unit and over the wash column rose within this period from 108 mbar to 120 mbar.

In thermodynamic model calculations (ASPEN PLUS V7.2), it was shown that about 1.6% of the phosgene conducted through the gas conduit was precipitated in the liquid. For this purpose, a gaseous stream at 170° C. consisting of 20% by weight of phosgene, 15% by weight of HCl and 65% by weight of o-dichlorobenzene was mixed with a liquid stream at 85° C. consisting of 97.5% by weight of o-dichlorobenzene and 2.5% by weight of tolylene diisocyanate in a mixer. Analogously to the experiment, the weight ratio was set to 1:2 (o-dichlorobenzene:gas stream). The calculated temperature of the mixture was 157° C. as in the experiment. The mixed stream was then separated into a gaseous stream and a liquid stream at 1.5 bar(a) in a "Flash2" without further supply or removal of heat, and the distribution of the phosgene between these two streams was examined.

The invention claimed is:

1. A process for separating an organic isocyanate prepared by reacting an organic amine with a stoichiometric excess of phosgene in the gas phase from the gaseous crude product obtained in the reaction, the process comprising the steps of
   (i) at least partially condensing the crude product stream containing at least the isocyanate, hydrogen chloride and unconverted phosgene by contacting with at least one liquid stream containing at least one quench liquid in a first separation apparatus to obtain
      a liquid stream containing at least some of the quench liquid and some of the isocyanate and
      a gas stream containing at least hydrogen chloride, evaporated quench liquid and phosgene,
   (ii) discharging the liquid stream obtained in step (i) via a first liquid outlet and of the gas stream obtained in (i) via a first gas conduit and
   (iii) at least partially condensing and/or absorbing the gas stream discharged in step (ii) through the first gas conduit,
wherein at least partial condensation and/or absorption is effected in step (iii) by direct introduction of at least one cooling fluid, wherein the cooling fluid is introduced directly into the first gas conduit via at least one addition unit assigned to the first gas conduit.

2. The process as claimed in claim 1, wherein the weight ratio of the cooling fluid introduced to the gas stream conducted through the first gas conduit is 1:100 to 10:1.

3. The process as claimed in claim 1, wherein the cooling fluid is selected to correspond to the solvent used as quench liquid in step (i).

4. The process as claimed claim 1, further including the steps of
   (iv) separating the gas stream from the first gas conduit in a second separation unit into a liquid stream and a gas stream and
   (v) recycling the liquid stream obtained in step (iv) as quench liquid via a second liquid conduit into the first separation unit.

5. The process as claimed in claim 1, wherein the cooling fluid is selected from the group consisting of chlorobenzene, o-di chlorobenzene, p-dichlorobenzene, trichlorobenzenes, the corresponding chlorotoluenes or chloroxylenes, chloroethylbenzene, monochlorodiphenyl, α- or β-naphthyl chloride, ethyl benzoate, dialkyl phthalates, diisodiethyl phthalate, toluene and/or xylene, preferably chlorobenzene, o-dichlorobenzene and p.

6. The process as claimed in claim 1, wherein the addition unit establishes a lowering of the temperature in the gas stream by 0.5 to 50 K.

* * * * *

UNITED STATES PATENT AND TRADEMARK OFFICE
CERTIFICATE OF CORRECTION

PATENT NO. : 11,279,670 B2
APPLICATION NO. : 17/146628
DATED : March 22, 2022
INVENTOR(S) : Manfred Kobylka et al.

It is certified that error appears in the above-identified patent and that said Letters Patent is hereby corrected as shown below:

In the Claims

In Column 18, at Line 24, please remove the space in "o-di chlorobenzene".

In Column 18, at Line 28-29, please cancel "preferably chlorobenzene, o-dichlorobenzene and p".

Signed and Sealed this
Tenth Day of May, 2022

Katherine Kelly Vidal
Director of the United States Patent and Trademark Office